(12) United States Patent
Levy et al.

(10) Patent No.: US 8,697,155 B2
(45) Date of Patent: Apr. 15, 2014

(54) TREATMENT OF OBESITY AND RELATED DISORDERS

(75) Inventors: Michael J. Levy, Rochester, MN (US); Mark D. Topazian, Rochester, MN (US); Steven P. Petrou, Ponte Vedra Beach, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 330 days.

(21) Appl. No.: 13/055,009

(22) PCT Filed: Jul. 20, 2009

(86) PCT No.: PCT/US2009/051137
§ 371 (c)(1),
(2), (4) Date: Jan. 25, 2011

(87) PCT Pub. No.: WO2010/011597
PCT Pub. Date: Jan. 28, 2010

(65) Prior Publication Data
US 2011/0130783 A1    Jun. 2, 2011

Related U.S. Application Data

(60) Provisional application No. 61/082,595, filed on Jul. 22, 2008.

(51) Int. Cl.
| | | |
|---|---|---|
| A61K 35/00 | (2006.01) | |
| A61K 38/48 | (2006.01) | |
| A61M 29/00 | (2006.01) | |
| A61K 38/00 | (2006.01) | |
| A61P 3/04 | (2006.01) | |

(52) U.S. Cl.
USPC .............. 424/780; 606/191; 514/4.8; 514/1.1

(58) Field of Classification Search
None
See application file for complete search history.

(56) References Cited

U.S. PATENT DOCUMENTS

| | | | | |
|---|---|---|---|---|
| 5,437,291 A * | 8/1995 | Pasricha et al. | ............... | 128/898 |
| 6,201,014 B1 | 3/2001 | Gardiner | | |
| 7,666,912 B2 * | 2/2010 | Grosskreutz et al. | ......... | 514/622 |
| 2004/0009224 A1 * | 1/2004 | Miller | ........................... | 424/484 |
| 2005/0175636 A1 * | 8/2005 | Donovan | ................... | 424/239.1 |
| 2005/0196440 A1 | 9/2005 | Masters et al. | | |
| 2005/0214325 A1 | 9/2005 | David | | |
| 2006/0073182 A1 * | 4/2006 | Wong et al. | ................... | 424/426 |
| 2008/0139641 A1 | 6/2008 | Meyer | | |

FOREIGN PATENT DOCUMENTS

| | | |
|---|---|---|
| WO | WO 02/13854 | 2/2002 |
| WO | WO 2007/106727 | 9/2007 |

OTHER PUBLICATIONS

Jacob et al. (1986) Pharmacology of DMSO. Cyrobiology, 23, No. 1, pp. 14-27.*
Sandborn et al. (2006) Ann. NYAS 243.1: 122-138.*
Albanese et al. (1995) Aliment. Pharmacol. Ther. 9: 599-604.*
Miller et al. (2002) Am. J. Gastroenterology vol. 97, No. 7 pp. 1653-1660.*
International Preliminary Report on Patentability, dated Jan. 25, 2011.
Notification of Transmittal of the International Search Report and the Written Opinion of the International Searching Authority, or the Declaration, dated Mar. 9, 2010.
Topazian et al., "Endoscopic Ultrasound-Guided Gastric Botulinum Toxin Injections in Obese Subjects: A Pilot Study", Obes. Surg., 2008, 18:401-407.
Chen et al., "Effect of Dimethyl Sulfoxide on Bladder Tissue Penetration of Intravesical Paclitaxel", Clin. Cancer Res., 2003, 9:363-369.
Pierson et al., "Botulinum Toxin A in the Treatment of Spasticity: Functional Implications and Patient Selection", Arch. Phys. Med. Rehabil., 1996, 77:717-721.
Jankovic et al., "Longitudinal experience with botulinum toxin injections for treatment of blepharospasm and cervical dystonia", Neurology, 1993, 43: 834-836.
Schantz et al., "Properties and Use of Botulinum Toxin and Other Microbial Neurotoxins in Medicine", Microbiol. Rev., 1992, 56(1):80-99.
"Clinical Use of Botulinum Toxin", National Institutes of Health Consensus Development Conference Statement, Nov. 12-14, 1990. Arch. Neurol., 1991, 48:1294-1298.
Scott et al., "Systemic Toxicity of Botulinum Toxin by Intramuscular Injection in the Monkey", Mov. Disord., 1988, 3:333-335.

* cited by examiner

*Primary Examiner* — Chris R Tate
*Assistant Examiner* — Russell Fiebig
(74) *Attorney, Agent, or Firm* — Fish & Richardson P.C.

(57) ABSTRACT

This disclosure provides a method of treating obesity and related disorders through the administration of a composition comprising a neurotoxin and a mucosal permeabilizing agent. Methods for making and using the described compositions are also provided.

11 Claims, 1 Drawing Sheet

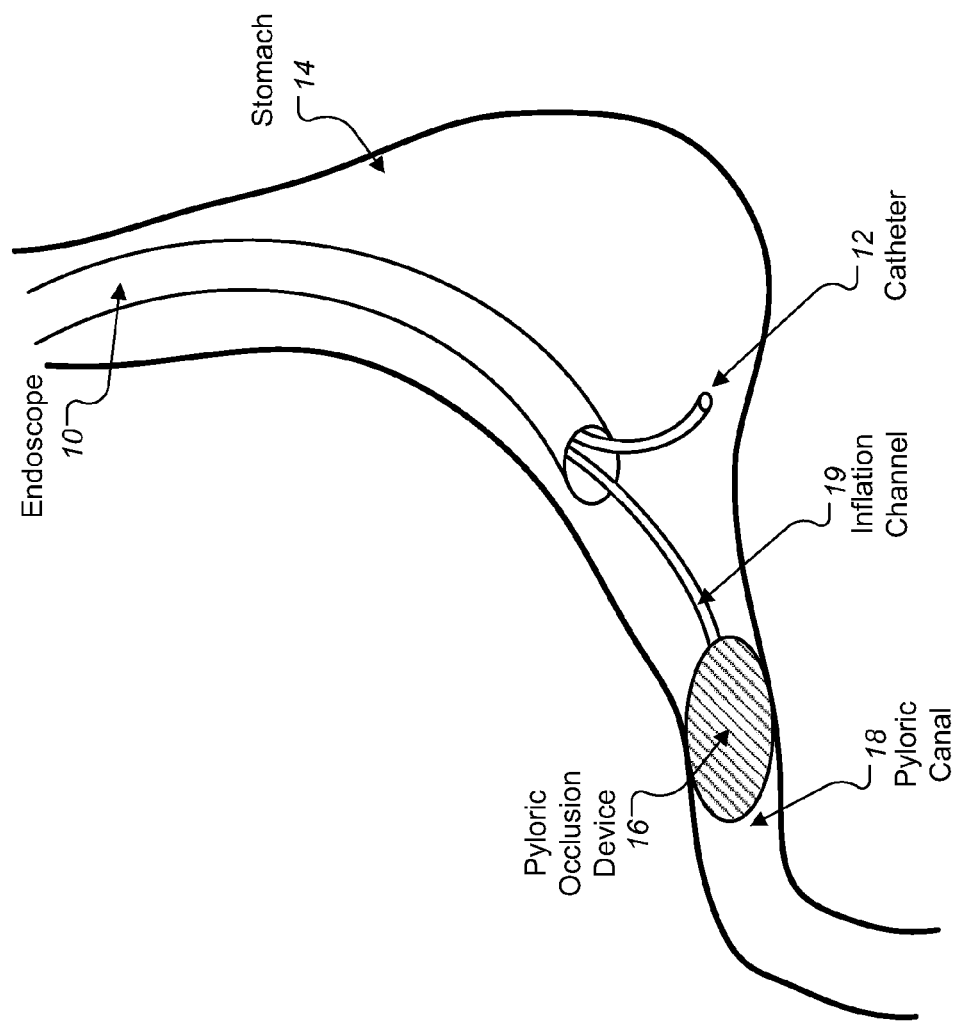

TREATMENT OF OBESITY AND RELATED DISORDERS

CROSS-REFERENCE TO RELATED APPLICATIONS

This application is a national phase application under 35 U.S.C. §371 of PCT International Application No. PCT/US2009/051137, filed Jul. 20, 2009, which claims the benefit under 35 USC 119(e) of U.S. Provisional Patent Application Ser. No. 61/082,595, filed on Jul. 22, 2008, which is incorporated herein by reference in its entirety.

TECHNICAL FIELD

This disclosure relates to a method for the treatment of obesity and gut motility disorders, and related disorders.

BACKGROUND

Obesity is a growing epidemic. According to a National Center for Health Statistics report, as of 2006, more than 33% of the male and female adult population of the United States suffers from obesity. In 2003, the Department of Human Health Services reported that obese and overweight adults cost the United States over 69 billion dollars per year.

In response to this growing epidemic, the use of botulinum toxin injections have been reported in the treatment of obesity. See, WO 2002/13854. Current methods rely on injection of botulinum toxin directly in the muscle layer of the stomach. This injection technique requires the use of an endoscope to get the injection needle to the appropriate muscle layer of the stomach. Preliminary research also suggests that botulinum toxin injections can relax stomach muscles to facilitate ease of deployment of the gastric Lap Band®. See, e.g., WO 2007/106727. It is, however, a challenge for the physician to confirm that the injection needle is within the muscle layer of the stomach, which may account for the variability in the published clinical results of injection of botulinum toxin to treat obesity. See, for example, Topazian et al., *Obes. Surg.*, 2008, 18:401-407. Furthermore, the gastric wall is thinner in the fundus and body as compared to the antrum. A treatment method that is capable of delivering the botulinum toxin without the potential complications associated with surgical procedures or the need for local, regional, or general anesthesia is desirable.

SUMMARY

Accordingly, the disclosure provided herein relates to a method of treating obesity and related disorders through the administration of a composition of matter. In one aspect of the disclosure, a composition of matter includes a neurotoxin such as botulinum toxin, a mucosal permeabilizing agent (MPA) such as dimethyl sulfoxide (DMSO), and one or more of a mucosal adhering agent such as sodium hyaluronate, a pH adjusting agent such as disodium hydrogen phosphate, a proton pump inhibitor such as omeprazole, an excipient such as starch, and a filler such as lactose.

In some embodiments, a neurotoxin can be selected from the group consisting of botulinum toxin, saxitoxin, tetanus toxin, capsaicin, resiniferatoxin, α-bungarotoxin, tetrodotoxin and other synthetic or natural neurotoxins.

In some embodiments, a neurotoxin (e.g., botulinum-A toxin or botulinum-B toxin) may be present at a dose of from about 100 to about 1,000 units, from about 200 to about 900 units, or from about 300 to about 800 units, or from about 400 to about 700 units, or from about 500 to about 600 units. In some embodiments, the botulinum toxin may be botulinum-A toxin or botulinum-B toxin.

In some embodiments, a mucosal permeabilizing agent may be DMSO or protamine sulfate. In some embodiments, the mucosal permeabilizing agent may be present from about 20 to about 90% by weight, from about 30 to about 80% by weight, from about 40 to about 70% by weight or at about 50% by weight. In some embodiments, the mucosal adhering agent may be selected from Methocel, Carbopol 934 P, sodium CMC, Polycarbophil (Noveon AA-1), HPMC, sodium alginate, sodium hyaluronate, or other synthetic or natural mucosal adhering agents.

In some embodiments, a pH adjusting agent may be selected from salts of acetate, citrate, tartarate, malate, fumarate, adipate, succinate, carbonate, bicarbonate, hydrogen phosphate, dihydrogen phosphate, or other synthetic or natural pH adjusting agents, or mixtures of such pH adjusting agents. In some embodiments, the proton pump inhibitor may be selected from rabeprazole, omeprazole, lansoprazole, pantoprazole, esomeprazole, or other synthetic or natural proton pump inhibitors and cogeners or their racemic mixtures.

In some embodiments, an excipient may be added to increase the viscosity of the composition of matter (e.g., a viscosity increasing agent). The viscosity increasing agent excipient may be selected from starches, polyoxyethylene glycols, polyethylene glycols, or lactose. In some embodiments, the excipient may be an emulsion-forming agent; an emulsion-forming agent in some embodiments is selected from long-chain fatty acids, partial glycerides and polyglycerides of fatty acids, saturated polyglycolized glyceride or other amphiphiles. In some embodiments, a filler may be selected from starches, lactose, sucrose, glucose, mannitol, silicic acid or other synthetic or natural fillers. In some optional embodiments, the composition including a neurotoxin and an MPA may include a radiopaque solution to discern the distribution pattern of the neurotoxin.

In some embodiments, the composition may be a solution (e.g., an aqueous solution). In some embodiments, the composition may be a gel. In some embodiments, the composition may be an emulsion. In some embodiments, the composition may be a solid dosage form (e.g., a tablet or caplet). In some embodiments, the composition may be a suspension.

In another aspect of the disclosure, a method of treating, preventing, or ameliorating one or more symptoms associated with obesity or a related disorder in a mammal is provided. A mammal may be, for example, a human, monkey, dog, cat, horse, sheep, cow, or pig. The method includes the administration of a therapeutically effective amount of a composition including a neurotoxin (e.g., botulinum toxin) and a mucosal permeabilizing agent (e.g., DMSO), thereby treating, preventing, or ameliorating one or more of the symptoms of obesity in the mammal. In some embodiments, the composition may be administered by oral ingestion of the composition by the mammal. In some embodiments the composition may be administered by direct instillation of the composition in the stomach of the mammal. In some embodiments, the oral ingestion may be in the form of a gel, an emulsion, an aqueous solution, a suspension, or a solid dosage form. In some embodiments, the direct instillation includes the use of a catheter, an endoscope, or a feeding tube.

In another aspect of the disclosure, a method of treating, preventing, or ameliorating one or more symptoms associated with obesity or a related disorder in a mammal (e.g., a human) is featured. The method may optionally include treating the mammal with a proton pump inhibitor or a pH adjusting agent followed by delivering a pyloric occlusion device (e.g., using an endoscope) to the pylorus of the mammal. A therapeutically effective amount of a composition including a neurotoxin and a mucosal permeabilizing agent may then be administered for a desired period of time, e.g., through an endoscope or catheter. The administered composition may then be neutralized or removed (e.g., after a desired time period) and the pyloric occlusion device may be removed.

In some embodiments, the neutralization may be performed with a neutralizing agent such as a peptidase, a reducing agent, an oxidizing agent, or a buffer. In some embodiments, the neutralization may be performed by removal of at least some portion of the residue of the administered composition, e.g., with an endoscope. In some embodiments, the pyloric occlusion device may be a balloon.

The disclosure also features a method of treating, preventing, or ameliorating one or more symptoms associated with obesity or related disorders in a mammal (e.g., a human). The method includes administering to the mammal a therapeutically effective amount of a composition of matter that includes from about 10% to about 60% by weight of DMSO and from about 100 to about 1,000 units of botulinum toxin (e.g., botulinum A toxin), thereby treating, preventing, or ameliorating one or more of the symptoms of obesity in the mammal. Administration of the composition can result in decreased weight or BMI in said mammal. The composition can be directly instilled into the stomach, e.g., administered through the use of a catheter or endoscope.

In another aspect of the present disclosure, a therapeutically effective amount of the DMSO/neurotoxin composition will be determined by the reduction in obesity symptoms (e.g., a decrease in BMI, weight loss, decreased waist circumference). Certain symptoms and/or indications of obesity may be those commonly associated with a body mass index (BMI) of 30 or higher.

The composition administered to the mammal may include DMSO present in an aqueous solution from about 20% to about 90% by weight (e.g., about 25% to about 90%, or about 50% by weight) of the solution, and botulinum toxin present from about 100 to about 700 units (e.g., about 300 units). In some embodiments, the botulinum toxin may be botulinum-A toxin (Botox®).

In certain embodiments, the composition can be administered to the stomach of the mammal. The composition can be administered directly into the stomach of a mammal through the use of a non-needle delivery system, e.g., direct instillation into the stomach. Administration of this sort may be accomplished through the use of an endoscope, a catheter or a feeding tube.

In another aspect of the present disclosure, any of the described compositions, such as compositions including a neurotoxin and an MPA, and the described methods may be used to treat, prevent, or ameliorate indications related to altered gut motility, e.g., dyspepsia, IBS, cyclic nausea and vomiting, achalasia, tenesmus, and post esophageal fundoplication complications.

Unless otherwise defined, all technical and scientific terms used herein have the same meaning as commonly understood by one of ordinary skill in the art to which this invention belongs. Although methods and materials similar or equivalent to those described herein can be used in practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1 demonstrates one embodiment of direct instillation of a composition described herein, where the embodiment employs the use of an endoscope, a catheter, and a pyloric occlusion device.

DETAILED DESCRIPTION

Obesity can be a result of either increased food consumption, lack of physical activity, genetic predisposition to decreased metabolism, or a combination thereof. Obesity is often linked to the development of diabetes, cardiovascular diseases, hypertension and certain cancers. The assessment of obesity is usually done with the determination of the Body Mass Index (BMI). Adults with a BMI of >25 are overweight, those with a BMI of >30 are classified as obese and those with a BMI>40 are classified under clinically severe obesity (morbid obesity). In certain borderline cases, the determination of waist circumference can become an additional indication. Current treatment for obesity consists of either medical or surgical approaches. Medical treatments include both medications and dietary restrictions. Surgical procedures are usually recommended for patients with morbid obesity and can involve the use of a Lap Band® procedure or a gastric by-pass surgery.

Compositions of Matter

Provided herein are methods and compositions for treating, preventing, or ameliorating one or more symptoms associated with obesity, e.g., a BMI of >30, in a mammal. The methods can include administering a therapeutically effective amount of a composition comprising a neurotoxin, a mucosal permeabilizing agent, and one or more of a mucosal adhering agent, a pH adjusting agent, a proton pump inhibitor, an excipient, and a filler to a mammal (e.g., a human).

A composition provided herein can include a neurotoxin. The neurotoxin in the composition can be highly selective, easy to deliver, and safe. Typically, a neurotoxin is included in an amount of from about 100 to about 1,000 units (e.g., from about 200 to about 900 units, from about 300 to about 800 units, or from about 400 to about 700 units, or from about 500 to about 600 units). Non-limiting examples of neurotoxin agents include botulinum toxin, saxitoxin, tetanus toxin, capsaicin, resiniferatoxin, α-bungarotoxin, and tetrodotoxin and other synthetic or natural neurotoxins. Suitable botulinum toxins include, for example, botulinum toxins A, B, C (C1 and C2), D, E, F, or G. Botulinum toxins A, B, and F are particularly useful.

Botulinum-A toxin is the most potent biological toxin known; it produces temporary muscular paralysis when injected locally. The neurotoxin acts as a selective inhibitor of acetylcholine release from pre-synaptic nerve endings. Botulinum-A toxin has been FDA approved since the 1980s for the treatment of focal dystonias such as blepharospasm, non-dystonic disorders such as hemi-facial spasms, disorders of conjugate eye movement such as strabismus and nystagmus, spasticity disorders such as multiple sclerosis and cerebral palsy, and for disorders of localized muscle spasm. In addition, botulinum-A toxin has been used to treat age related rhytids of the upper face. Botulinum-A toxin is safe and effective to use, and is relatively painless with rare side effects characterized as mild and transient. Onset of action takes place within 24 to 72 hours after injection and lasts 2 to 6 months. Botulinum-A toxin is available commercially, e.g., from Allergan, Inc. (Irvine, Calif., Botox®) and Speywood Pharmaceuticals (England, Dysport®). See, e.g., National Institutes of Health Consensus Development Conference Statement, Nov. 12-14, 1990. *Arch. Neurol.*, 1991, 48:1294; Jankovic, J. and Schwartx, K., *Neurology*, 1993, 43: 834; and Pierson, S., Katz, D., Torsy, D., *Arch. Phys. Med. Rehabil.*, 1996, 77:717.

Dosages of botulinum-A toxin vary widely depending on the size of the area to be treated. Primate studies have indicated that no systemic effects are observed at dosages below 33 units/kg body weight. See, for example, Scott and Suzuki, *Mov. Disord.*, 1988, 3:333-335.

Botulinum toxins also can be obtained by purifying the toxins from strains of *Clostridium botulinum*, using standard techniques. For example, botulinum-A toxin can be produced in a Hall strain using a nutritive medium containing casein digest, yeast extract, and dextrose. After lysis of the culture, the toxin is released into the medium and activated by proteases, and then is acid precipitated. Further purification can include extraction with a sodium phosphate buffer, ethanol precipitation, and crystallization in ammonium sulfate. See, for example, Schantz, E. J. and Johnson, E. A., *Microbiol. Rev.*, 1992, 56(1):80-99.

A composition provided herein can include a mucosal permeabilizing agent (MPA). While not intending to be bound by any particular theory, it is believed that a mucosal permeabilizing agent can assist in achieving transmission of the toxin to the muscle layer of the stomach. Typically, an MPA is included in an amount of from about 20% to about 90% (e.g., from about 30% to about 80%, from about 40% to about 60%, or about 50%) by weight of the composition. Non-limiting examples of mucosal permeabilizing agents include DMSO, protamine sulfate and other synthetic or natural mucosal permeabilizing agents. In one embodiment, DMSO is used as an MPA. In another embodiment, protamine sulfate is used as an MPA. Mixtures of any of the foregoing MPAs can also be employed. In some embodiments, DMSO is used in an amount of from about 20% to about 90% by weight of the composition; in some embodiments, DMSO is used in an amount of about 50% by weight of the composition.

DMSO is a widely used solvent with pharmacological actions including bacteriostatic activity, analgesia, vasodilation, diuresis, and muscle relaxation. Following topical application, DMSO is absorbed and generally distributed in the tissues and body fluids. See, e.g., Chen, D., Song, D., Wientjes, G., and Au, J. L-S., *Clin. Cancer Res.*, 2003, 9:363-369.

A composition provided herein can include a mucosal adhering agent. While not intending to be bound by any particular theory, it is believed that a mucosal adhering agent can assist in achieving transmission of the toxin to the muscle layer of the stomach. Typically, a mucosal adhering agent is included in an amount of from about 20% to about 90% (e.g., from about 30% to about 80%, from about 40% to about 60%, about 50%) by weight of the composition. Non-limiting examples of mucosal adhering agents include Methocel, Carbopol 934 P, sodium CMC, Polycarbophil (Noveon AA-1), HPMC, sodium alginate, sodium hyaluronate, and other synthetic or natural mucosal adhering agents. Mixtures of any of the foregoing mucosal adhering agents can also be employed.

A composition provided herein can include a pH adjusting agent. While not intending to be bound by any particular theory, it is believed that a pH adjusting agent can assist in modifying (e.g., reducing) the acidity levels of the stomach during the absorption of the neurotoxin and/or the mucosal permeabilizing agent. For example, in some embodiments, the pH adjusting agent will increase the pH of the stomach. Typically, a pH adjusting agent is included in an amount of from about 20% to about 90% (e.g., from about 30% to about 80%, from about 40% to about 60%, about 50%) by weight. Non-limiting examples of pH adjusting agents include salts of acetate, citrate, tartarate, malate, fumarate, adipate, succinate, carbonate, bicarbonate, hydrogen phosphate, dihydrogen phosphate, and other synthetic or natural pH adjusting agents. Mixtures of any of the foregoing pH adjusting agents can also be employed.

A composition provided herein can include a proton pump inhibitor (PPI). While not intending to be bound by any particular theory, it is believed that a PPI can prevent the production of acid in the stomach. This blocking can result in enhanced absorption of the neurotoxin and/or the mucosal permeabilizing agent. Typically, a PPI is included in an amount of from about 20 mg to about 150 mg (e.g., about 30, 40, 50, 60, 70, 80, 90, 100, 110, 120, 130, 140 mg) by weight. Non-limiting examples of PPIs include rabeprazole, omeprazole, lansoprazole, pantoprazole, esomeprazole, and other synthetic or natural proton pump inhibitors. Mixtures, racemic mixtures or cogeners of any of the foregoing PPIs can also be employed.

A composition provided herein can be in liquid, gel, emulsion, suspension form, a solution (e.g., aqueous solution), or solid dosage form. For example, in some embodiments, a gel or emulsion form of a composition can be employed, e.g., to minimize movement of the composition after localization in the stomach and to enhance localized permeabilization of the toxin. In some embodiments, e.g., wherein a pyloric occlusion device is employed as described below, a liquid, solution, emulsion or a suspension form can be employed.

In one embodiment, the composition includes botulinum-A toxin and DMSO in solution, e.g., aqueous solution. This solution may include from about 100 to about 1,000 units of botulinum-A toxin (e.g., 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1,000 units) and from about 20 to about 90% w/w solution of DMSO (e.g., 20%, 25%, 30%, 35%, 40%, 45%, 50%, 55%, 60%, 65%, 70%, 75%, 80%, 85%, or 90%). In some embodiments, the solution includes from about 40% to about 60% w/w solution of DMSO and from about 200 to about 500 units of botulinum-A toxin. The two components can be combined and stored, e.g., at 4° C., until used, or mixed prior to administration. For example, prior to administration, an appropriate amount of lyophilized botulinum-A toxin can be reconstituted with an appropriate solution of DMSO to result in a solution (e.g., an instillation) containing the desired final concentration of botulinum-A toxin and DMSO.

In certain embodiments, the composition comprising DMSO may include, for example, one or more of water, saline, aqueous dextrose, glycerol, glycols, ethanol, and the like, to thereby form a solution or suspension. If desired, the composition to be administered may also contain minor amounts of non-toxic auxiliary substances such as wetting agents, emulsifying agents, solubilizing agents, pH adjusting agents and the like, for example, acetate, sodium citrate, cyclodextrin derivatives, sorbitan monolaurate, triethanolamine, sodium acetate, triethanolamine oleate, and other such agents.

A composition or a method provided herein can include use of a tracer dye, e.g., a radiopaque agent, a scintigraphic agent, or an MRI contrast agent to discern the distribution pattern of the neurotoxin. Examples of radiopaque agents include barium sulfate, iodinated agents such as ioxaglates, triiodobenzoic acid, and its derivatives (like iodipamide, iopamidol, iomeprol, iohexyl, ioversol, iopentol, ioproide, ioxilan, iotriside, iobitridol, iodixanol, iofratol, iotrolan, iodecimol, iopirol, iopiperidol, iothalamate, or iohexyl), diatrizoates and other such agents. Examples of scintigraphic agents include $^{99m}$Tc salts such as pertechnetates, and $^{99m}$Tc-sulfur colloids. Examples of MRI contrast agents include ferumoxides; chelate of $Mn^{2+}$ with N,N'-bis(pyrodoxal-5-phosphate)ethylenediamine-N,N'-diacetic acid (Mn-DPDP); and chelates of $Gd^{3+}$ with diethylenetriamine pentaacetic acid (Gd-DTPA), [10-(2-hydroxypropyl)-1,7,10-tetraazacyclodecan-1,4,7-triacetic acid (Gd-HPD03A), 4-carboxy-5,8,11-tris(carboxy ethyl)-1-phenyl-2-oxa-5,8,11-triazamide-can-13-oic acid (Gd-BOPTA), 1,4,7,10-tetraazacyclododecan-1,4,7,10-tetraacetic acid (Gd-DOTA), N-[2-[bis(carboxymethyl)amino]-3-(-ethoxyphenyl)propyl]-N-(2-[bis(carboxy ethyl)amino] ethylglycine (Gd-EOB-DTPA), $(\alpha,\alpha',\alpha'',\alpha''')$-tetramethyl-1,4,7,10-tetraazocyclododecan-1,4,7,10-tetraacetic acid (Gd-DOTMA), and N,N-bis[2-[(carboxymethyl)[(methylcarbamoyl)methyl]amino]ethyl]-glycine (Gd-DTPA-BMA).

The compositions described above can be formulated as articles of manufacture, e.g., kits, containing the described compositions or components for preparing the described compositions. For example, in one embodiment, a kit may include separate containers, e.g., vials, of DMSO and botulinum-A toxin, for mixing prior to administration. In other embodiments, previously prepared solutions of DMSO and botulinum-A toxin may be included in a kit. Additional items such as packaging, labels including instructions, balloons, syringes, catheters, endoscopes, and other equipment necessary or useful for administration can be included.

The compositions described above are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active composition sufficient to produce the desired therapeutic effect, in association with any required pharmaceutical excipients. These excipients may be, for example, to increase the viscosity of the composition, such as starches, polyoxyethylene glycols, polyethylene glycols, or lactose; for example, emulsion-forming agents, such as long-chain fatty acids, partial glycerides and polyglycerides of fatty acids, saturated polyglycolized glyceride, and other amphiphiles; for example, fillers, such as starches, lactose, sucrose, glucose, mannitol, or silicic acid; for example, inert diluents, such as calcium carbonate, sodium carbonate, lactose, calcium phosphate or sodium phosphate; for example, granulating and disintegrating agents, such as, maize starch, or alginic acid; binding agents, for example, starch, gelatin or acacia; and for example, lubricating agents, such as magnesium stearate, stearic acid or talc. The tablets may be uncoated or may be coated by known techniques to delay disintegration and absorption in the gastrointestinal tract and thereby provide a sustained action over a longer period. For example, a time delay material such as glyceryl monostearate or glyceryl distearate may be employed. Other excipients are listed in Handbook of Pharmaceutical Excipients, 2nd edition, which is incorporated herein by reference in its entirety. Unit-dose forms may be administered in fractions or multiples thereof. A multiple-dose form is a plurality of identical unit-dosage forms packaged in a single container to be administered in segregated unit-dose form.

Actual methods of preparing such dosage forms are known, or will be apparent, to those skilled in this art; for example, see Remington's Pharmaceutical Sciences, Mack Publishing Company, Easton, Pa., 15th Edition, 1975.

Methods of Use

Also described are methods for treating, preventing, or ameliorating one or more symptoms associated with obesity or a related disorder in a mammal (e.g., a human). The methods can employ a composition comprising a neurotoxin as described previously and a mucosal permeablizing agent as described previously. In certain aspects of this application, a composition comprising a neurotoxin and a MPA is a composition described previously, e.g., a composition which further comprises one or more of a mucosal adhering agent, a pH adjusting agent, a proton pump inhibitor, an excipient, and a filler.

Similarly, methods for treating, preventing, or ameliorating indications related to altered gut motility, e.g., dyspepsia, IBS, cyclic nausea and vomiting, achalasia, tenesmus, and post esophageal fundoplication complications are also described. These methods The methods can employ a composition comprising a neurotoxin as described previously and a mucosal permeablizing agent as described previously. In certain aspects of this application, a composition comprising a neurotoxin and a MPA is a composition described previously, e.g., a composition which further comprises one or more of a mucosal adhering agent, a pH adjusting agent, a proton pump inhibitor, an excipient, and a filler.

Administration of a composition comprising a neurotoxin and an MPA or any of the previously described compositions may include administering an amount of about 100 to about 1,000 mL (e.g., 100, 200, 300, 400, 500, 600, 700, 800, 900, or 1,000 mL) of a solution (e.g., an aqueous solution), liquid, gel, emulsion, or a suspension form including from about 100 to about 1,000 units of neurotoxin and from about 20 to about 90% w/w solution of a mucosal permeabilizing agent.

Current administration of botulinum-A toxin utilizes laparoscopic or endoscopic guided injections in the stomach lining and/or muscle. While no permanent systemic side effects have been noted, there is a transient injection site discomfort associated with the process and it requires the use of anesthesia. Furthermore, the endoscopic guided injections only allow focal delivery of compositions. While not intending to be bound by any particular theory, it is believed that agents and methods described herein may allow more uniform delivery, which can be useful when attempting to have a significant effect on the gastric wall where non-treated areas could overcome the inhibition of function that would occur with only focused treatment. In certain embodiments, a composition comprising a neurotoxin (e.g., botulinum-A toxin) and an MPA (e.g., DMSO) may be delivered into the stomach through guided injections into the stomach (rather than to the stomach lining and/or muscle).

In other embodiments of the present method, a composition comprising a neurotoxin and an MPA (and optionally further comprising one or more of a mucosal adhering agent, a pH adjusting agent, a proton pump inhibitor, an excipient, and a filler) is delivered by direct instillation into the stomach (e.g., through a catheter, or a feeding tube based delivery system). This latter delivery method may limit the potential complications associated with surgical procedures or anesthesia. The use of a catheter may also permit the delivery of the composition specifically to either the upper (fundus) or the lower part (antrum) of the stomach.

In some optional embodiments, the mammal (e.g., a human) can be treated with a proton pump inhibitor or a pH adjusting agent, e.g., at a time period prior to, during, or after the administration of the composition. The mammal (e.g., a human) can then be subjected to insertion of an endoscope 10 (e.g., including a catheter 12) into the stomach 14. In some optional embodiments, a pyloric occlusion device 16 (e.g., a balloon) can be placed at the pyloric (duodenal) canal 18 and inflated via the inflation channel 19. This pyloric occlusion device 16 can prevent the spillage of the composition (e.g., an instillate) into the small bowels and hence prevent its paralysis. The composition including the neurotoxin and mucosal permeabilizing agent can then be administered for a period of time through the catheter 12. In some optional embodiments, the administered composition can then be neutralized (e.g., after a desired time period) either by the removal of the administered composition via the endoscope (e.g., a gastroscope) or by neutralization with specific agents such as, but not limited to, a peptidase, a reducing agent, an oxidizing agent, or a pH adjusting agent. A pyloric occlusion device 16 can be removed using the endoscope 10.

A catheter delivery system is an effective means to deliver medications directly into the stomach. A treatment through the delivery of the composition by direct stomach instillation allows for direct pumping of a therapeutic composition into the stomach through a endoscopic (e.g., a gastroscopic) catheter. The composition, e.g., DMSO and botulinum-A toxin, is held in the stomach for a "dwell time" before the administered composition is neutralized. This procedure allows the treatment of the stomach wall directly with high concentrations of medication for dwell times ranging from 1 minute to 1 hour.

The use of direct ingestion by a mammal (e.g., oral ingestion) of a composition can also be a method for delivery of the composition to the stomach. Such a composition can be in liquid, gel, suspension, emulsion or solid dosage form. In some embodiments, a composition may be coated, e.g., to prevent its absorption before the composition reaches the stomach, where it is then selectively released.

In some optional embodiments, the composition comprising a neurotoxin and an MPA may be delivered into the stomach followed by the introduction of a gastric band such as Lap Band® around the stomach, with the gastric band being introduced for the purpose of regulating food intake in a clinically severe obese mammal.

As used herein, treatment means any manner in which one or more of the symptoms of a disease or disorder are ameliorated or otherwise beneficially altered. Treatment also encompasses any pharmaceutical use of the compositions herein, such as use for treating diseases or disorders in which the composition is implicated.

As used herein, amelioration of the symptoms of a particular disorder by administration of a particular compound or pharmaceutical composition refers to any lessening, whether permanent or temporary, lasting or transient that can be attributed to or associated with administration of the composition.

The composition may be administered at once, or may be metachronously dosed, e.g., to be administered at intervals of time. It is understood that the precise dosage and duration of treatment is a function of the severity of the disease being treated and may be determined empirically using known testing protocols or by extrapolation from in vivo or in vitro test data. It is to be further understood that for any particular subject, specific dosage regimens should be adjusted over time according to the individual need and the professional judgment of the person administering or supervising the administration of the compositions.

To evaluate the effectiveness of an obesity treatment, gastric emptying of solids (by scintigraphy using $^{99m}$Tc-sulfur colloid), satiation (by maximum tolerated volume (MTV) during nutrient drink test), gastrointestinal symptoms (by the gastrointestinal symptom rating scale), caloric intake (using the Three Day Nutrition/Cholesterol Control Receptor questionnaire), and improvements in the patient's weight, BMI, and/or waist circumference can be measured by the use of accepted measurement protocols known to those having ordinary skill in the art. See, for example, Topazian et al., Obes. Surg., 2008, 18:401-407.

The invention is further described in the following examples, which do not limit the scope of the invention described in the claims.

EXAMPLES

Example 1

A composition of botulinum-A toxin and DMSO is prepared by combining 100 to 1,000 units of botulinum toxin Type A and 50 to 100 mL of dimethyl sulfoxide in a 10-90% w/w aqueous solution.

Example 2

A composition consisting of botulinum-A toxin and DMSO is prepared by combining 200 to 900 units of botulinum toxin Type A and 50 to 100 mL of dimethyl sulfoxide in a 10-90% w/w aqueous solution.

Example 3

A group of three patients suffering from symptoms of obesity will undergo stomach instillation of 50 mL of the composition as described in Example 1. Patients will be chosen based on the results of baseline weight and BMI measurements.

The composition will be administered using diagnostic upper endoscopy. A flexible video endoscope will be introduced to the stomach. The pylorus will be occluded with a balloon catheter passed via the endoscope, or separately over a guidewire. The composition will be instilled with gravity pressure, left in the stomach lumen for a variable time period, and then the composition will be neutralized by either suction removal of the residual composition or the use of neutralizing agents. The pyloric occlusion balloon will then be removed. Patients will be monitored 24 hours and one week after the initial instillation and then at post-procedure intervals of 1 and 3 months.

Effectiveness of the composition will be evaluated by weight, BMI and/or waist circumference measurements.

Example 4

A similar study, as detailed in Example 3, will be conducted. A group of 25 patients with symptoms of obesity will undergo stomach instillation of the composition as described in Example 2. The initial examination, administration, and evaluation of this study will be conducted as described above.

A number of embodiments of the invention have been described. Nevertheless, it will be understood that various modifications may be made without departing from the spirit and scope of the invention. Accordingly, other embodiments are within the scope of the following claims.

What is claimed is:
1. A method for the treatment of obesity in a mammal in need thereof comprising
administering directly into the stomach by gastric intubation of said mammal a therapeutically effective amount of a composition comprising a botulinum toxin and a mucosal permeabilizing agent.

2. The method of claim 1, wherein said administering comprises the use of a catheter, an endoscope, or a feeding tube.

3. The method of claim 1, wherein the composition further comprises a neurotoxin selected from the group consisting of saxitoxin, tetanus toxin, capsaicin, resiniferatoxin, α-bungarotoxin, and tetrodotoxin.

4. The method of claim 1, wherein said botulinum toxin is botulinum-A toxin or botulinum-B toxin.

5. The method of claim 1, wherein said mucosal permeabilizing agent is selected from the group consisting of DMSO and protamine sulfate.

6. The method of claim 1, wherein the mammal is a human.

7. The method of claim 1, wherein said composition further comprises one or more agents selected from the group consisting of a mucosal adhering agent, a pH adjusting agent, a proton pump inhibitor, an excipient, and a filler.

8. A method for the treatment of obesity in a mammal in need thereof comprising
   administering directly into the stomach by gastric intubation of said mammal a therapeutically effective amount of an aqueous composition comprising
      about 10% to about 60% by weight DMSO and about 100 to about 1,000 units of botulinum toxin.

9. The method of claim 8, wherein said botulinum toxin is botulinum-A toxin.

10. The method of claim 6, wherein administration of said composition results in decreased BMI in said human.

11. The method of claim 8, wherein said composition is administered through the use of a catheter.

\* \* \* \* \*

UNITED STATES PATENT AND TRADEMARK OFFICE
CERTIFICATE OF CORRECTION

PATENT NO. : 8,697,155 B2
APPLICATION NO. : 13/055009
DATED : April 15, 2014
INVENTOR(S) : Levy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 331 days.

Signed and Sealed this

Twenty-ninth Day of September, 2015

Michelle K. Lee
*Director of the United States Patent and Trademark Office*